(12) United States Patent
Khoury (10) Patent No.: US 12,186,178 B2
(45) Date of Patent: Jan. 7, 2025

(54) DIRECT SOFT TISSUE FIXATION IMPLANTABLE DEVICE AND METHOD OF USE

(71) Applicant: David J. Khoury, Jackson Hole, WY (US)

(72) Inventor: David J. Khoury, Jackson Hole, WY (US)

( * ) Notice: Subject to any disclaimer, the term of this patent is extended or adjusted under 35 U.S.C. 154(b) by 364 days.

(21) Appl. No.: 17/615,777

(22) PCT Filed: Jun. 2, 2020

(86) PCT No.: PCT/US2020/035705
§ 371 (c)(1),
(2) Date: Dec. 1, 2021

(87) PCT Pub. No.: WO2020/247373
PCT Pub. Date: Dec. 10, 2020

(65) Prior Publication Data
US 2022/0218464 A1  Jul. 14, 2022

Related U.S. Application Data

(60) Provisional application No. 62/856,593, filed on Jun. 3, 2019.

(51) Int. Cl.
*A61F 2/08* (2006.01)

(52) U.S. Cl.
CPC ..... *A61F 2/0811* (2013.01); *A61F 2002/0817* (2013.01); *A61F 2002/0864* (2013.01); *A61F 2002/0888* (2013.01); *A61F 2230/001* (2013.01); *A61F 2230/0065* (2013.01)

(58) Field of Classification Search
CPC ............ A61F 2/0811; A61F 2002/0817; A61F 2002/0864; A61F 2002/0888; A61F 2230/001; A61F 2230/0065
See application file for complete search history.

(56) References Cited

U.S. PATENT DOCUMENTS

| | | | | |
|---|---|---|---|---|
| 5,042,285 | A * | 8/1991 | Levy | H05K 13/0092 72/409.14 |
| 5,108,431 | A * | 4/1992 | Mansat | A61F 2/0811 623/13.14 |
| 5,571,104 | A * | 11/1996 | Li | A61F 2/0811 606/232 |
| 5,669,917 | A * | 9/1997 | Sauer | A61B 17/0487 606/232 |
| 5,968,044 | A * | 10/1999 | Nicholson | A61B 17/0401 606/301 |

(Continued)

*Primary Examiner* — Ryan J. Severson
(74) *Attorney, Agent, or Firm* — Mitchell J. W. Vap (57) ABSTRACT

Disclosed herein is a device and method for securing soft tissue such as the long head of the biceps tendon (or similar) as well as free grafts or allografts directly to bone. The device is directly crimped to the preferred soft tissue. This is accomplished by the application of a crimping device to the implantable device and application of sufficient force to crimp the implantable device thereby fixing said device to the tissue in question. The complex of the device and the tissue/tendon can then be directly fixed to bone as necessary. Additionally, the same device and method can be used to connect one tendon to another as indicated.

21 Claims, 13 Drawing Sheets

(56) References Cited

U.S. PATENT DOCUMENTS

| | | | | |
|---|---|---|---|---|
| 6,106,556 | A * | 8/2000 | Demopulos | A61B 17/1146 |
| | | | | 606/328 |
| 6,395,010 | B1 * | 5/2002 | Wotton, III | A61B 17/0487 |
| | | | | 606/103 |
| 8,900,302 | B2 * | 12/2014 | Gonzalez-Hernandez | ................. |
| | | | | A61F 2/0811 |
| | | | | 623/13.15 |
| 9,101,462 | B2 * | 8/2015 | Miller | A61F 2/0811 |
| 10,070,874 | B2 * | 9/2018 | Laviano | A61B 17/1631 |
| 10,085,830 | B2 * | 10/2018 | Spenciner | A61B 17/1764 |
| 10,675,141 | B2 * | 6/2020 | Greenhalgh | A61F 2/0811 |
| 11,918,454 | B2 * | 3/2024 | Spenciner | A61F 2/08 |
| 2004/0068262 | A1 * | 4/2004 | Lemos | A61F 2/0811 |
| | | | | 606/908 |
| 2004/0236374 | A1 * | 11/2004 | Bonutti | A61B 17/0487 |
| | | | | 606/232 |
| 2005/0234460 | A1 * | 10/2005 | Miller | A61F 2/0811 |
| | | | | 606/232 |
| 2010/0222792 | A1 * | 9/2010 | Barnes | A61F 2/0811 |
| | | | | 606/232 |
| 2012/0150296 | A1 * | 6/2012 | Miller | A61F 2/0811 |
| | | | | 623/13.14 |
| 2013/0060333 | A1 * | 3/2013 | Gonzalez-Hernandez | ................. |
| | | | | A61F 2/0811 |
| | | | | 623/13.15 |
| 2017/0079769 | A1 * | 3/2017 | Greenhalgh | A61F 2/08 |
| 2018/0049755 | A1 * | 2/2018 | Laviano | A61B 17/1714 |
| 2022/0192816 | A1 * | 6/2022 | Spenciner | A61B 17/0401 |
| 2022/0218464 | A1 * | 7/2022 | Khoury | A61F 2/0811 |

* cited by examiner

DIRECT SOFT TISSUE FIXATION IMPLANTABLE DEVICE AND METHOD OF USE

CROSS-REFERENCE TO RELATED APPLICATIONS

This application claims the benefits of U.S. Provisional Application No. 62/856,593, filed on Jun. 3, 2019, the disclosure of which is hereby incorporated by reference in its entirety including all figures, tables, and drawings.

STATEMENT REGARDING FEDERALLY SPONSORED RESEARCH OR DEVELOPMENT

Not applicable

THE NAMES OF THE PARTIES TO A JOINT RESEARCH AGREEMENT

Not applicable.

REFERENCE TO SEQUENCE LISTING, A TABLE, OR A COMPUTER PROGRAM LISTING COMPACT DISC APPENDIX

Not applicable.

BACKGROUND OF THE INVENTION

The present invention relates to surgical fixation devices and methods of surgical soft tissue fixation. More specifically, the device disclosed herein is an implantable device to secure soft tissue to bone or soft tissue to soft tissue, which is accomplished by direct contact between the device and tissue to be secured or fixated without the use of sutures or other fixation components. Also disclosed are methods of using the herein described device.

There are many devices and methods disclosed in the art to achieve soft tissue fixation to bone, or other soft tissue. For example, various embodiments of a "button" fixation device have been described for fixating soft tissue to bone. See U.S. Ser. No. 10/070,874; Buchholz et al., *Biomechanical Comparison of Intramedullary Cortical Button Fixation and Interference Screw Technique for Subpectoral Biceps Tenodesis*. Arthroscopy: The Journal of Arthroscopic and Related Surgery, Vol. 29, No. 5 (May 2013). However, all embodiments of "button" fixation devices require a suture connection from the device to the soft tissue to be fixated. Soft tissue-suture-device connections require a high degree of skill for a surgeon to perform. Furthermore, tissue quality can significantly affect the strength of the soft tissue-suture-device connection. Patients with poor tissue quality exhibit higher instances of loss of fixation and surgical failure. Similarly, the delicate soft tissue to suture connection associated with such devices requires a prolonged protective phase post-surgery to allow for sufficient physiologic healing and fixation stability prior to initiating rehabilitation of the repaired tissue. It is well described in the literature that early rehabilitation after surgery generally improves surgical outcomes.

Another device and technique utilized for soft tissue fixation is the use of an interference screw. An interference screw requires a suture to screw connection between the tissue to be fixated and the interference screw. Fixation is accomplished by engaging the threads of the interference screw in a bony tunnel, thus creating the anchor point for the soft tissue-suture-screw connection. Similar to the cortical "button" described above, interference screws require a suture connection between the device and soft tissue to be fixated. See Buchholz et al. supra. Furthermore, interference screws require purchase of threads into bone, which can potentially damage bone and is susceptible to loosening.

Similarly, U.S. Pat. No. 5,571,104 describes a surgical anchor and method of use where the device consists of a body with a plurality of barbs, which engage a bony tunnel to secure soft tissue to bone. The 104' device includes an opening to receive a loop of tendon, a loop of suture, or a bone block or plug. As such, the device requires enough free tendon or ligament to create a loop back onto itself for fixation to the device, a bone block or plug, or a suture to fix the device to the soft tissue.

U.S. Pat. No. 9,101,462 describes various devices and a method for preventing retraction of biological tissue during resection. The engaging element of the 462' patent includes at least two cooperating parts for trapping the first biological soft tissue and an anchor to interact with the second biological tissue. As such, the system described in the 462' patent requires surgical placement of two components and a mechanism or suture to connect the two components.

Various other crimping, clamping, and anchoring devices exist in the art, but suffer from the same shortcomings as the devices described previously. See U.S. Pat. No. 8,900,302 (tendon crimp requires suture); U.S. Pat. No. 5,968,044 (bone fastener requires suture or knot for tissue-device connection); U.S. Pat. No. 5,108,431 (clamp sleeve for artificial ligament utilizes internal saw tooth segments to engage ligament); WO 2008/017834 (Aglet compressed onto soft tissue, but requires suture to fixate); and U.S. Pat. No. 6,106,556 (splice consisting of reinforcing member and plurality of pins).

One common orthopaedic surgical procedure involves treating disease of the long head of the biceps and/or tearing at its proximal origin. Releasing the tendon (tenotomy) is an acceptable treatment option but has some potential side effects and occasionally results in a cosmetic deformity. The present preferred treatment is to subsequently reattach the long tendon of the biceps to the proximal humerus after tenotomy in the shoulder joint. There are a number of commercially available implants to accomplish this goal, some of which have been described above.

Because of the above described problems evident in the prior art, a need remains for an implantable device to secure tendon to bone or tendon to tendon, which is accomplished by direct contact between the tissue to device and tissue to be secured. The present device presents a novel approach to achieve this goal with relative ease and speed, both desirable attributes during surgery. There are also other advantages compared to current devices (interference screws, expandable anchors, metal implants attached via sutures) including use of a smaller cortical socket thereby reducing risk of subsequent bone fracture, minimizing inventory, circumferential tendon to bone healing, avoidance of graft disruption upon implant deployment, and avoiding suture creep or knot failure.

BRIEF SUMMARY OF THE INVENTION

Provided is the description of a novel implantable device with direct attachment to the soft tissue or tendon in question via a novel crimping method using a novel crimping device. The implantable device is comprised of material, which surrounds the diameter of soft tissue or tendon, and is affixed directly to the soft tissue or tendon by crimping the device with the tendon/tissue passed through the device, thereby providing secure fixation of the device to the tendon/tissue without the use of suturing. Once affixed to the tendon/tissue, the implant can be inserted into the medullary canal of a bone, such as the proximal humerus, through a unicortical socket sized to precisely match the tendon/tissue diameter. The socket is made with widely available techniques and instruments. Matching tendon diameter to the unicortical socket provides for circumferential healing of the tendon/tissue-bone connection, increased stability of the fixation, and less healing time of the repair. Typically, other fixation devices described above must utilize a considerably larger socket than the tendon/tissue diameter to accommodate the implant, which risks subsequent fracture due to the larger socket size, decreased stability, and potentially inadequate healing and/or longer healing durations. Once inserted beyond the cortex, the device is rotated 90 degrees so that the crimped device ends are held against the fixation surface, or medullary wall by the resting tension of the fixated soft tissue. Once inserted, the device will no longer fit back through the socket, effectively fixing the tendon inside the bone.

A preferred embodiment of the device is utilized for reattachment of soft tissue to bone. The typical steps include: (1) releasing the soft tissue from its insertion or origin point; (2) making a small incision and dissection to approach the fixation point for site preparation; (3) Measuring the diameter of the soft tissue to be fixated at or just distal to the musculotendinous junction; (4) drilling a corresponding unicortical socket to match the measured soft tissue diameter; (5) applying the implantable device to the soft tissue at the appropriate location; (6) crimping said implantable device with crimping pliers to appropriate force; (7) resecting the remainder of the proximal or distal soft tissue; and (8) inserting the crimp/soft tissue construct into the unicortical socket by rotating the crimp/soft tissue construct 90 deg. to clear the cortical wall of the unicortical socket and de-rotating the crimp/tendon construct to abut against the inner medullary wall. Another preferred embodiment of the method if using the device is further comprised of the step of doubling back of the tissue onto itself and reinserting the resected end of said tissue back through the device, which provides for increased tissue thickness for the device to crimp onto.

Another preferred embodiment of the implantable device is comprised of an oval ring with a lengthwise opening of approximately 8 mm and a width opening of approximately 6 mm. Said device is approximately 2 mm wide and is preferably made of any acceptable material suitable for implantation and structurally capable of resisting deformation once crimped. Titanium, or surgical stainless are the preferred materials; however, any implantable material capable of the herein described specifications could be used. Furthermore, said device could be sized or shaped to accommodate any morphology of tissue, where application of the device would be appropriate. For example, another preferred embodiment of the device is comprised of a circular-ring, sized to accommodate the tissue to be fixated.

Another preferred embodiment of the implantable device is comprised of a multiple opening device, which would allow for the tendon/tissue to be fixated to be inserted through a first opening and then doubled back and passed back through the a second opening of the device to achieve multiple crimps of the device on the tendon/tissue to increase fixation strength.

Another preferred embodiment is comprised of a crimping pliers device designed to accept the described implantable device. Each opposing jaw of said crimping pliers will have a longitudinal recessed groove to accept the implantable crimp device. The pliers will have a preset endpoint determined by tissue diameter to provide sufficient force to crimp the implantable device securely to the soft tissue but prevent excessive force and tissue damage.

While specific embodiments are provided herein, one skilled in the art would appreciate that the described device could be used for virtually any procedure requiring soft tissue fixation to bone. Furthermore, the described device could comprise any shape or size to accommodate different soft tissue morphology.

Due to the problems identified in the prior art regarding soft tissue-bone fixation devices and methods, it is an object of the present invention to provide a direct soft tissue-bone fixation device. It is another object of the present invention to provide a fixation device where the unicortical socket utilized with the device is the same diameter as the soft tissue to be fixated. It is another object of the present invention to provide a soft tissue-bone fixation device and method that reduces the risk of fixation site fracture, graft disruption upon implant deployment, and avoids suture creep or knot failure. It is another object of the present invention to provide a fixation device that minimizes prolonged post-surgical protection prior to initiating rehabilitation. It is a further object of the present invention to provide a direct soft tissue-soft tissue connection.

DETAILED DESCRIPTION OF THE INVENTION

Embodiments of the present invention will now be described more fully with reference to the accompanying drawings. As shown in FIGS. 4-9, the implantable device is comprised of a material structurally capable of resisting deformation once crimped. Said device is sized and shaped in a manner to insert a resected tendon or other tissue end through an interior opening of said device. Said interior opening is defined by an interior border of the material of said device. The device is also comprised of an exterior border, which is accepted by a specialized crimping tool, which crimps said device to said tendon/tissue. The implantable device can be sized and shaped in any manner to accommodate different sizes and morphologies of tissues. Furthermore, said interior and exterior borders can be further comprised of features to enhance purchase of the implantable device on the tissue/tendon once crimped.

Figure 4:
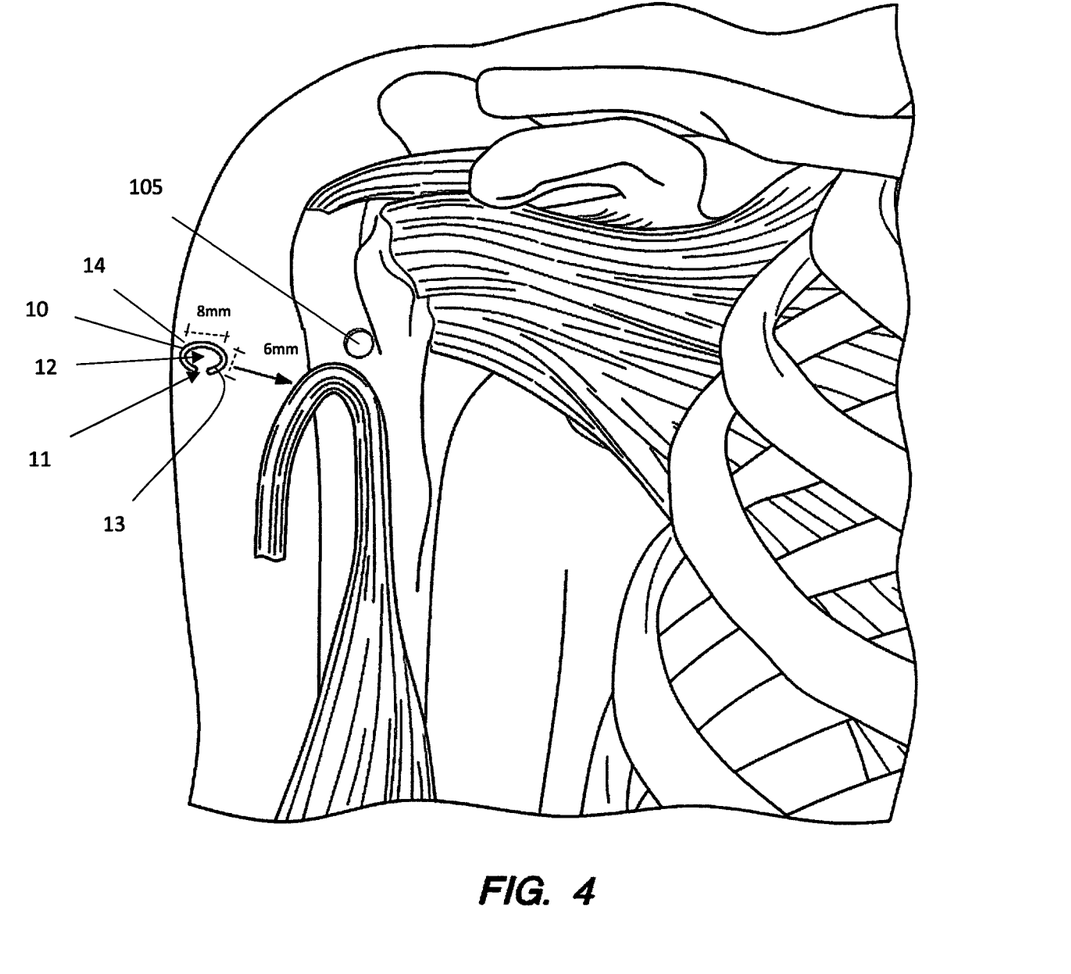
FIG. 4 illustrates application of a preferred device around the resected tendon.
Figure 5:
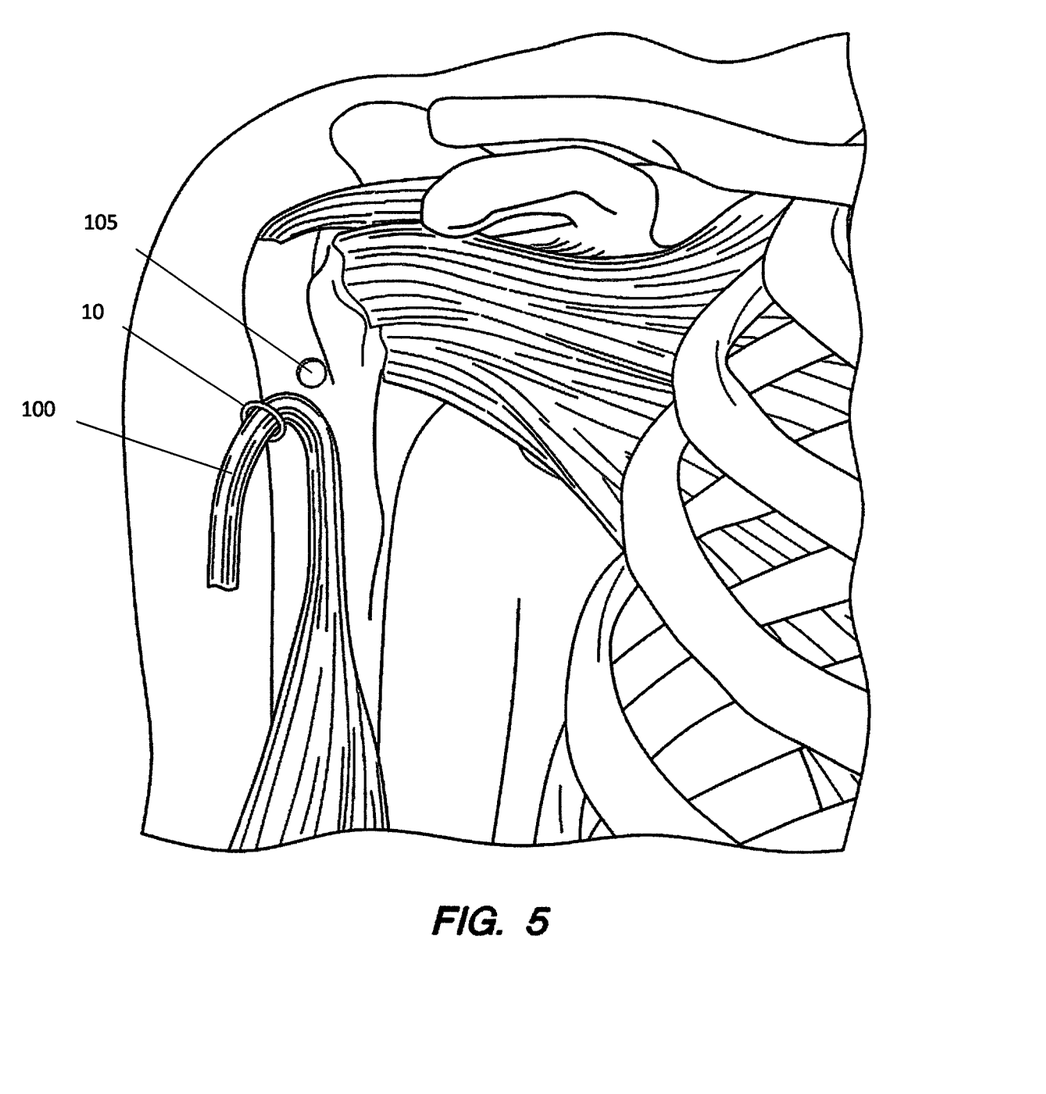
FIG. 5 shows device placed around the resected tendon, prior to crimping.

One preferred embodiment of the implantable device is comprised of an oval ring 10. Said oval ring can be a complete contiguous oval, or an incomplete oval comprised of a gap 11 to aid in affixing the device to the tissue/tendon at issue. One familiar with the art would recognize that the implantable device could be comprised of various shapes to accommodate tissues of any shape or size. Said oval ring 10 is comprised of an interior opening 12, which accommodates the tendon to be fixated. Said interior opening is defined by an interior border 13, which can be compete or incomplete as shown in FIG. 4. Said device is further defined by an exterior border 14, which is accepted by a specialized crimping pliers for crimping. Said exterior border 14 can be complete or incomplete as shown in FIG. 4.

The implantable device is preferably made of any acceptable material suitable for implantation and structurally capable of resisting deformation once crimped. Titanium, or surgical stainless are the preferred materials; however, any implantable material capable of the herein described specifications could be used. One of the preferred embodiments of said implantable device oval ring 10 is comprised of an interior opening 12 length of approximately 8 mm and a width of approximately 6 mm as shown on FIG. 4. The material portion of said device is approximately 2 mm in diameter. However, the device could be sized for application to any tendon/tissue size and/or morphology. For example, another preferred embodiment of the device is comprised of a circular ring, sized to accommodate the diameter of tissue to be fixated. The interior border 13 of said implantable device oval ring opening 12 can be further comprised of texturing, studs, barbs, or similar means to increase purchase of the implantable device on the tissue/tendon once crimped. The exterior border 14 of said implantable device can be further comprised of features to enhance purchase of said device to a fixating structure or surface. For example, said exterior border could be comprised of barbs, hooks, wings, or texturing to enhance purchase of the device to a fixation surface such as bone once implanted.

Figure 1:
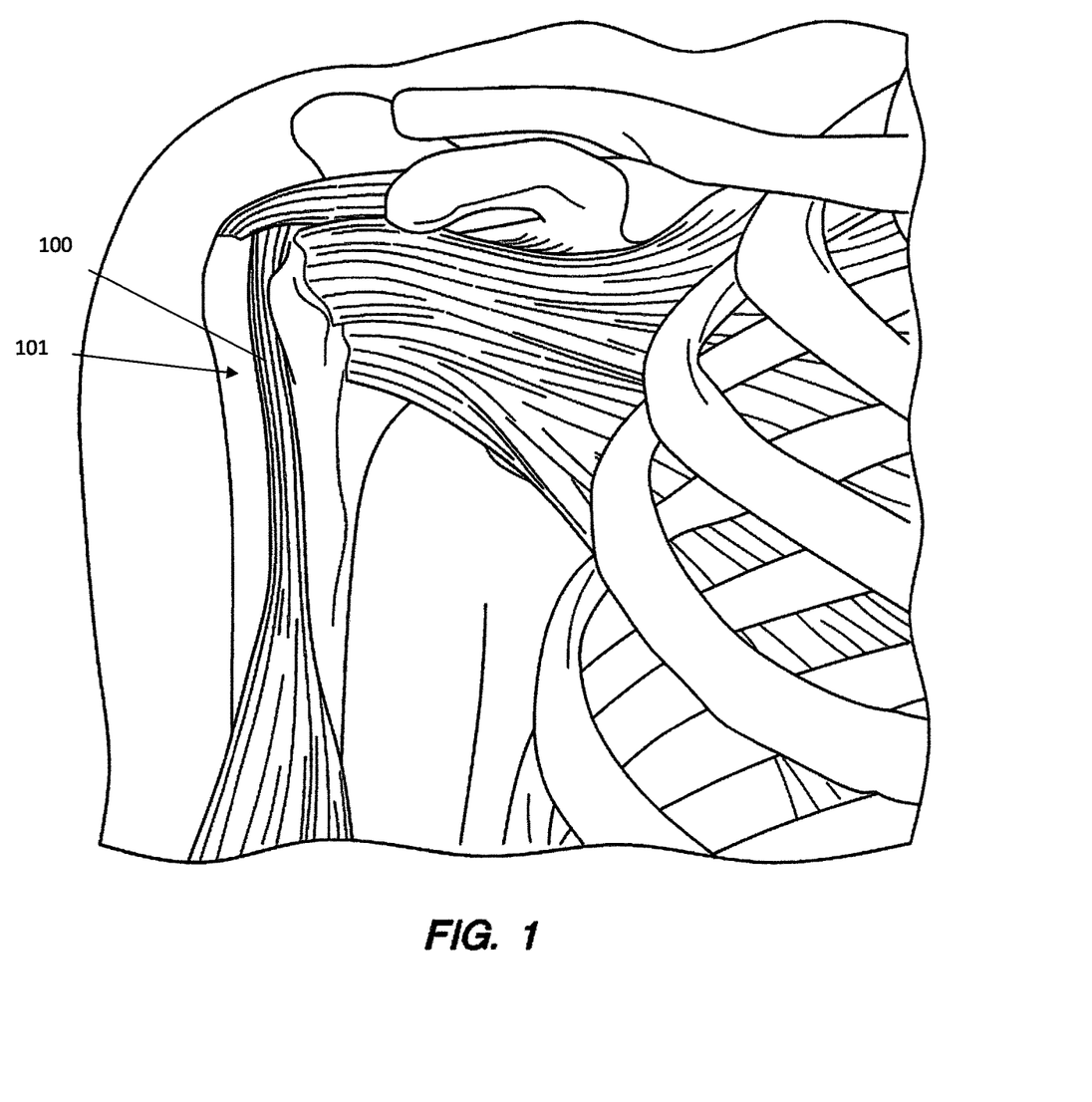
FIG. 1 is an anatomical representation of the anterior shoulder, proximal humerus, and long head of the bicep tendon.
Figure 2:
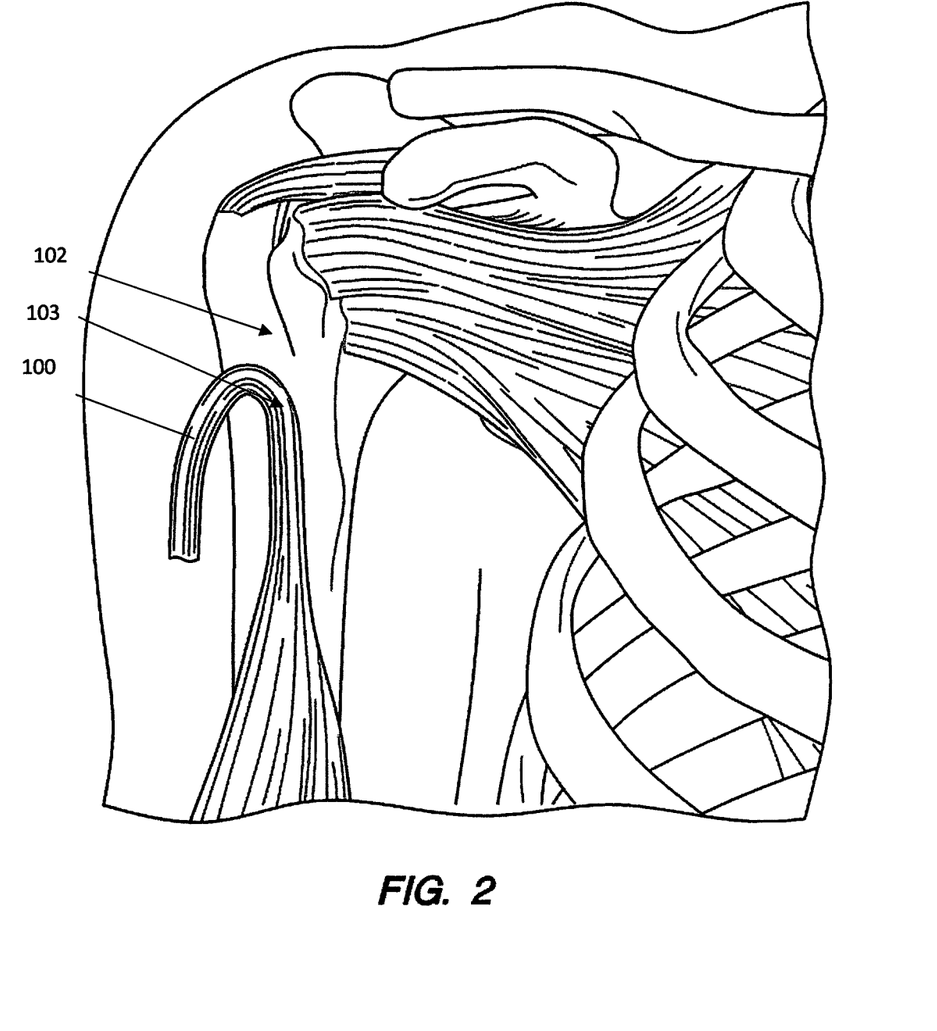
FIG. 2 is an anatomical representation of a resected long head of biceps tendon.
Figure 3:
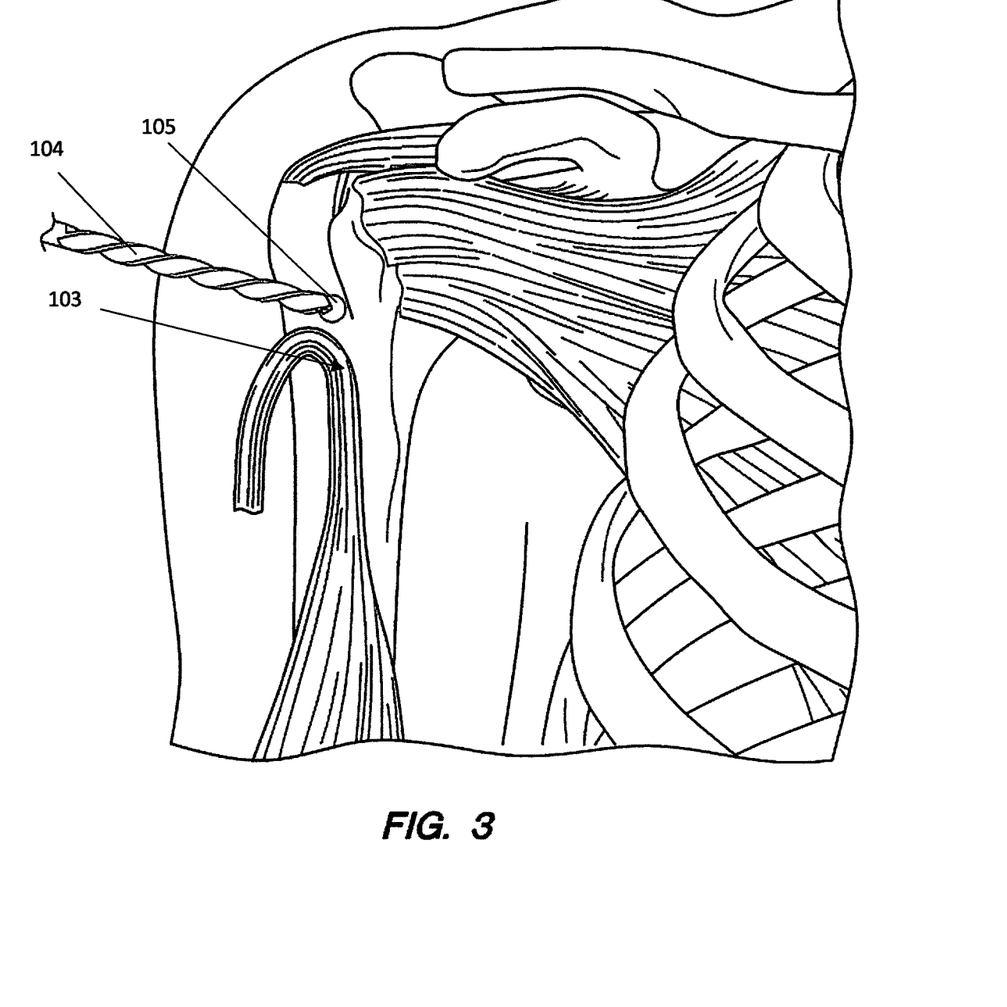
FIG. 3 illustrates drilling of a unicortical socket during a preferred method.
Figure 6:
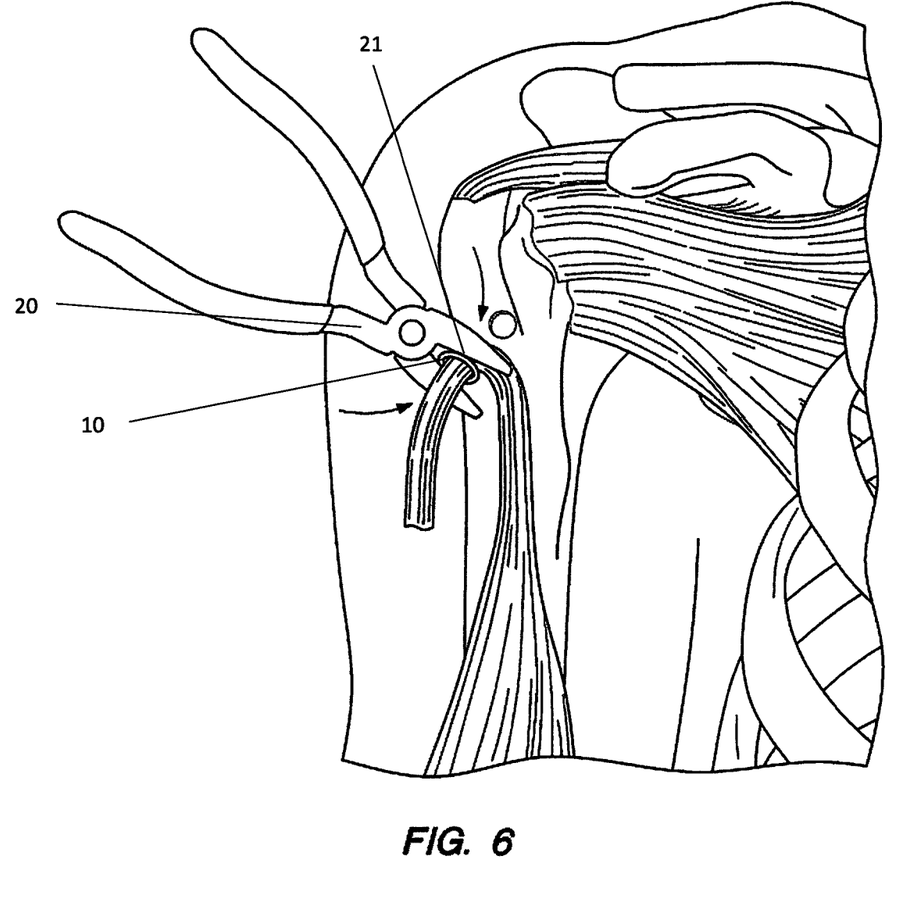
FIG. 6 demonstrates crimping of the device to resected tendon to create the crimp/tendon construct.
Figure 7:
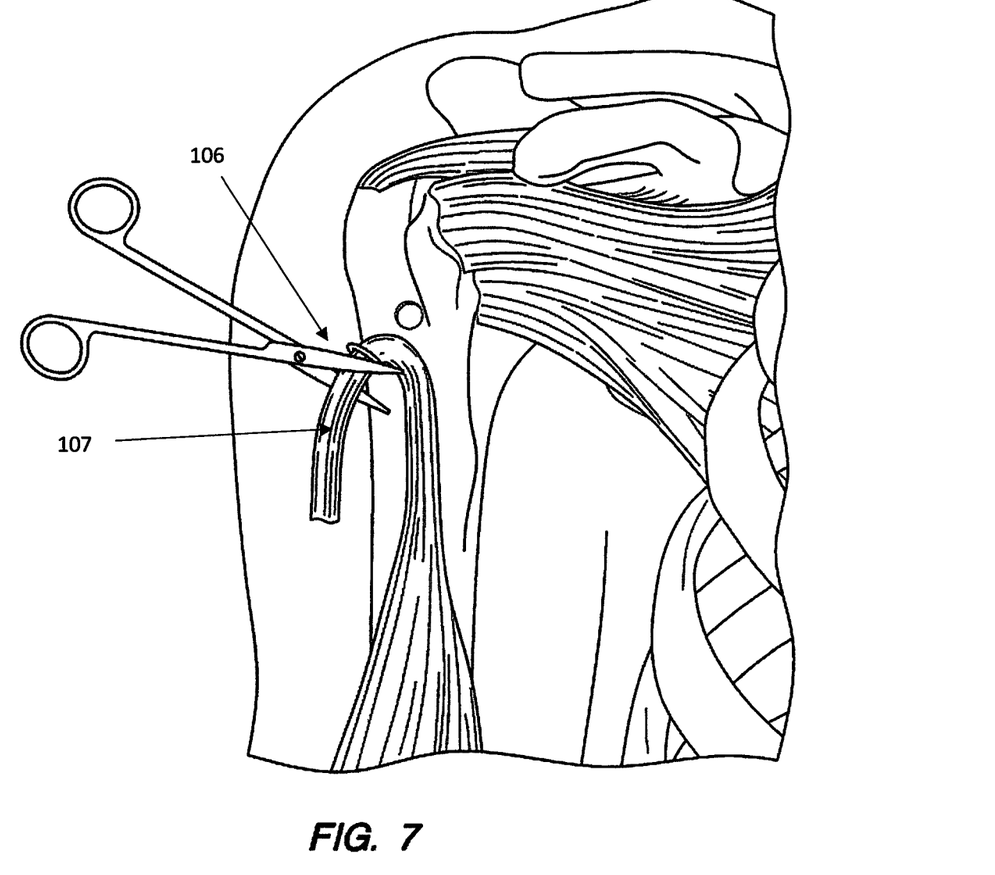
FIG. 7 demonstrates trimming of resected portion of tendon proximal to crimped device.
Figure 8:
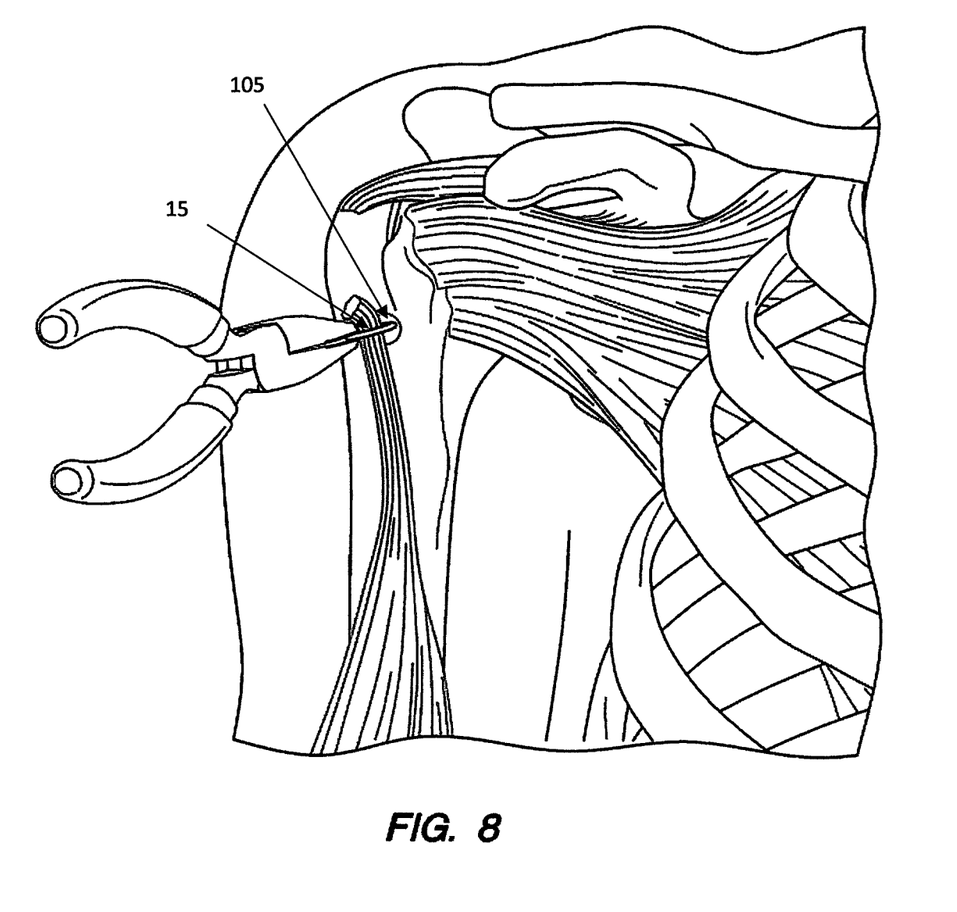
FIG. 8 demonstrates installation of the crimp/tendon construct by rotating device 90 degrees to insert device into unicortical socket.
Figure 9:
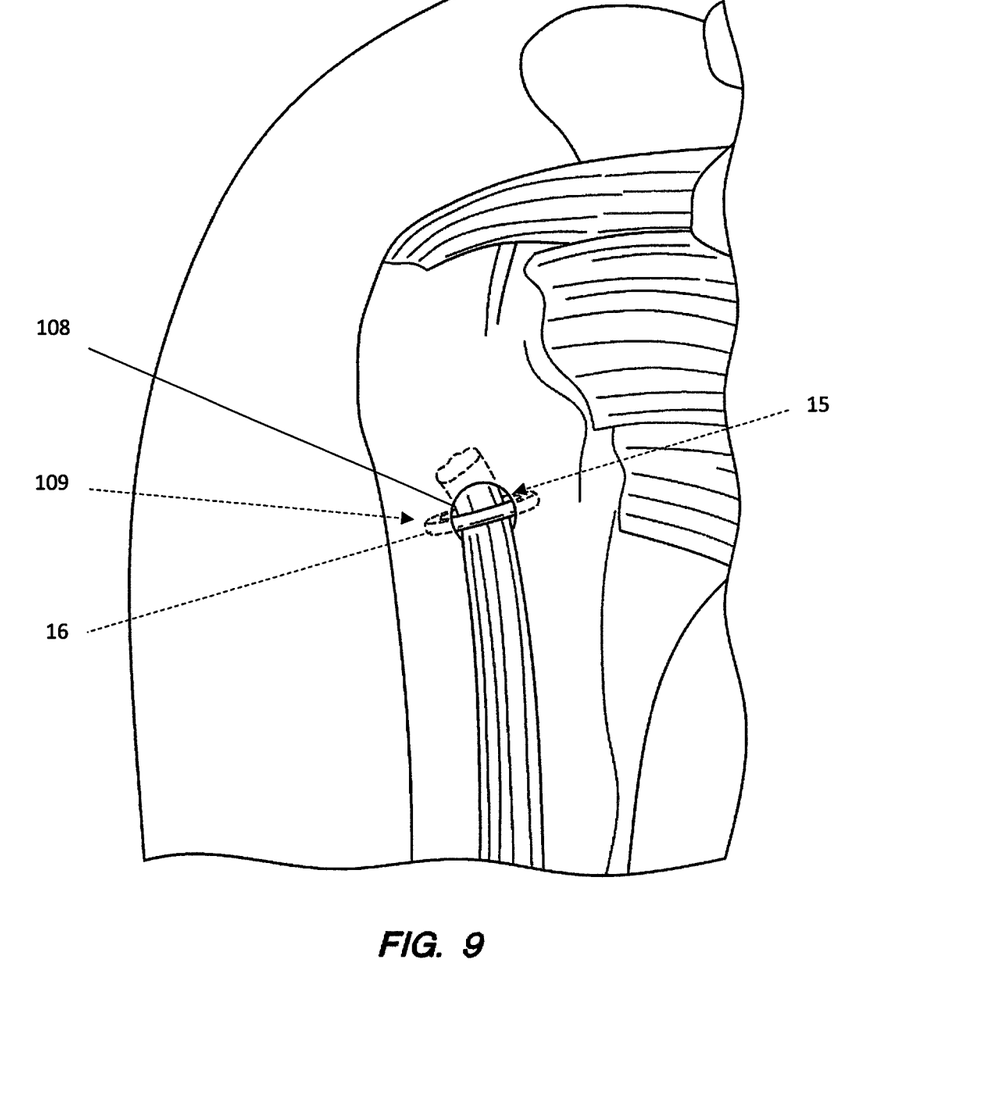
FIG. 9 demonstrates installed crimp/tendon construct where device is de-rotated 90 degrees to abut against the medullary wall.

A preferred embodiment of the implantable device oval ring 10 is utilized for reattachment of the long head of the biceps tendon 100 to the proximal humerus 101 after tenotomy FIG. 2 in the shoulder joint. The typical steps include: (1) releasing the long head biceps 100 from the labrum arthroscopically (for tearing of the biceps, SLAP tear, subscapularis repair, or any other conditions treated with biceps tenodesis); (2) making a small incision and dissection to approach the intertubercular portion 102 of the humerus at the inferior margin of the pectoralis major; (3) Measuring the diameter 103 of the long head of the biceps tendon 100 at or just distal to the musculotendinous junction (anatomic studies suggest restoration of correct length by tenodesing the tendon near the musculotendinous junction at a location immediately proximal to the inferior border of the pectoralis major); (4) drilling 104 a corresponding unicortical socket 105 to match the tendon diameter 103 (FIG. 3); (5) applying the implantable oval ring 10 to the long head of the biceps tendon 100 at the appropriate location (FIG. 5) by inserting said tendon into said opening 12; (6) crimping said implantable oval ring 10 with crimping pliers 20 to appropriate force (FIG. 6); (7) resecting 106 the remainder of the proximal tendon 107 (FIG. 7); and (8) inserting the crimp/tendon construct 15 into the unicortical socket 105 by rotating the crimp/tendon construct 15 90 deg. (FIG. 8) to clear the cortical wall 108 of the unicortical socket 105 and de-rotating the crimp/tendon construct 14 to abut against the fixation surface of the inner medullary wall 109 (FIG. 9). Once inserted, the crimped implantable oval ring 10 ends 16 are held against the fixation surface such as a medullary wall 109 by the resting tension of the fixated soft tissue.

Figure 10:
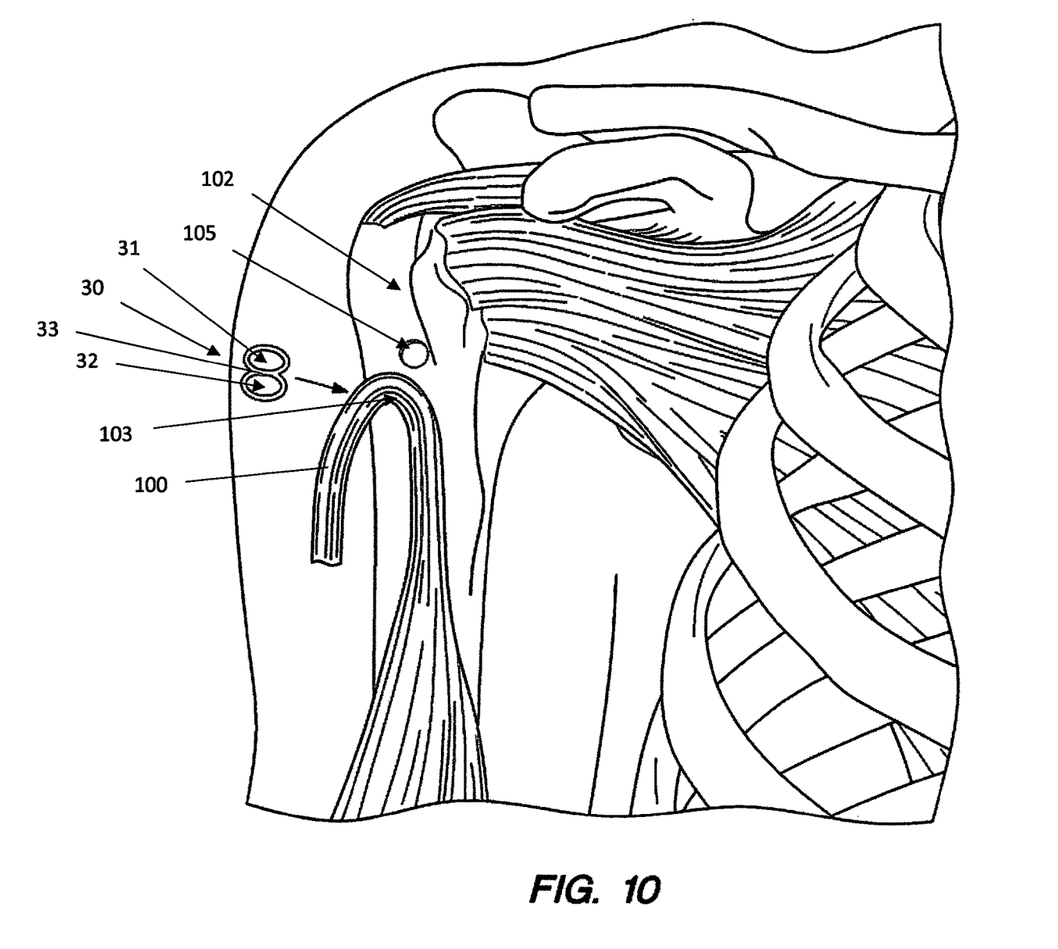
FIG. 10 illustrates application of another preferred implantable device with multiple openings prior to application to a resected tendon.
Figure 11:
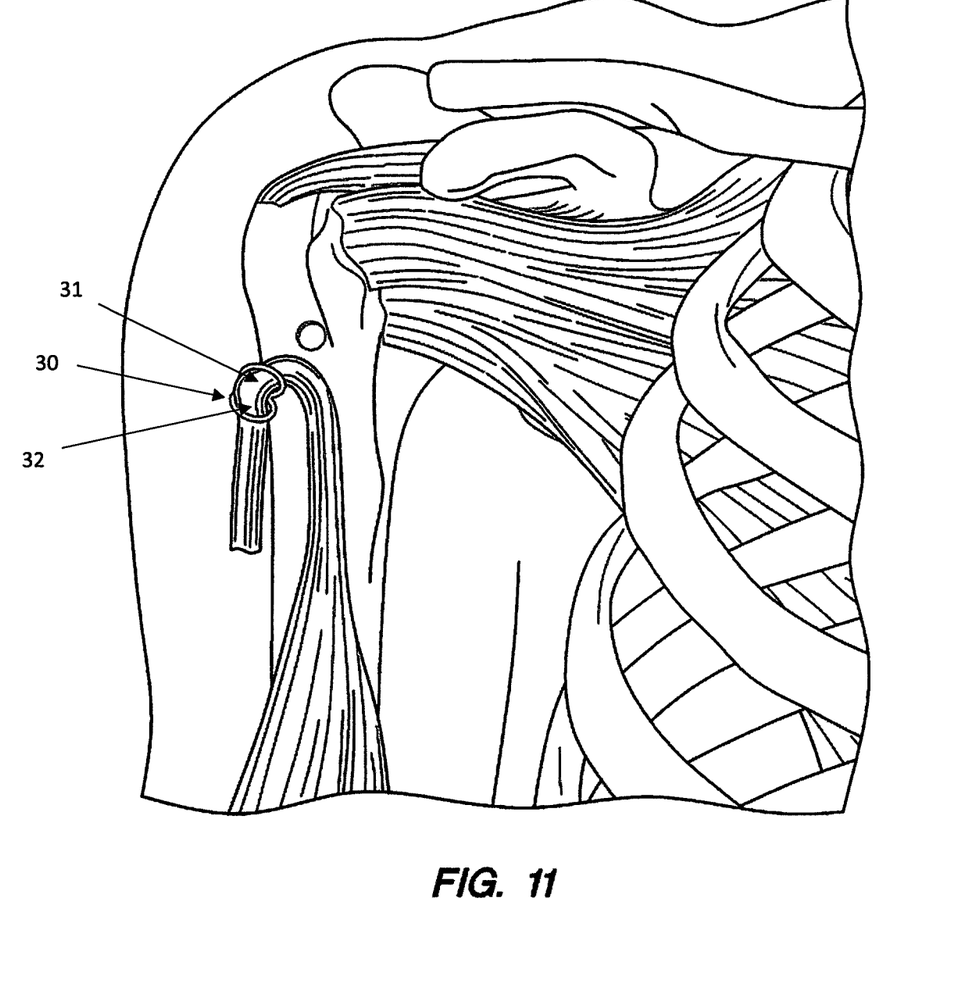
FIG. 11 shows the multi-opening embodiment of the implantable device placed around the resected tendon, prior to crimping. Tendon through first opening and back through second opening.
Figure 12:
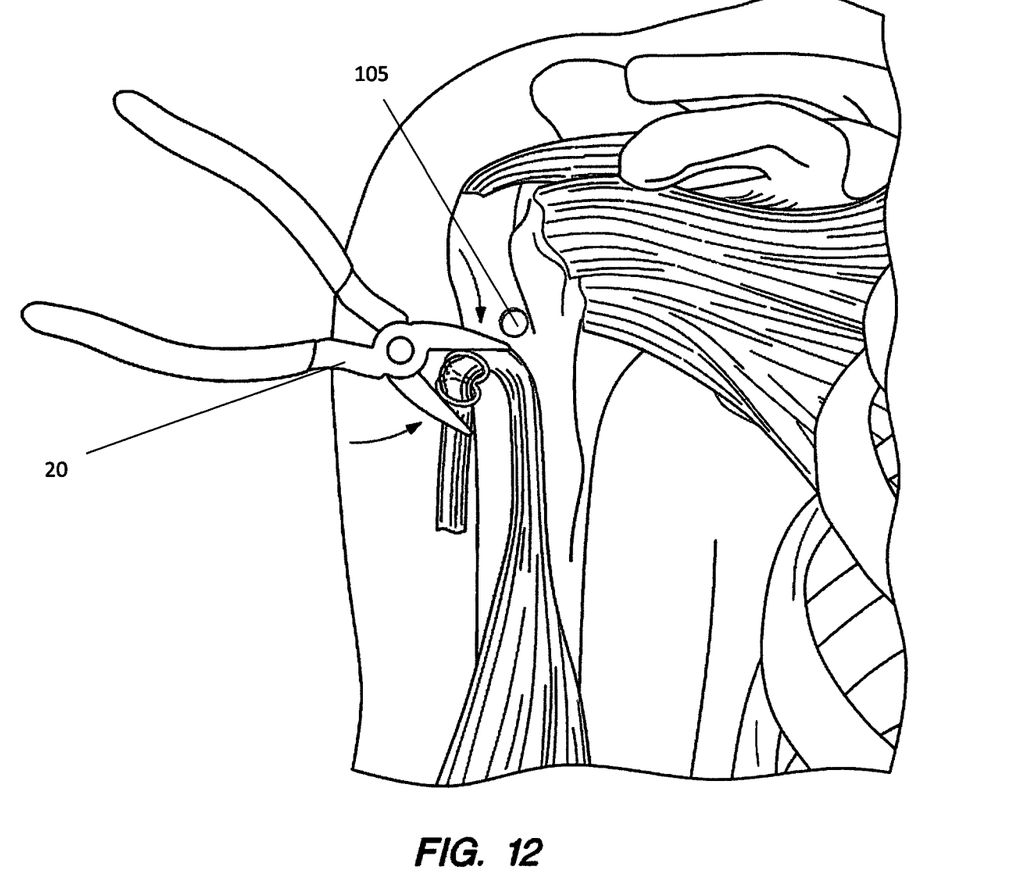
FIG. 12 demonstrates crimping of the multi-opening implantable device to resected tendon to create the crimp/tendon construct. Two crimps of doubled back tendon achieves greater device retention and fixation strength.
Figure 13:
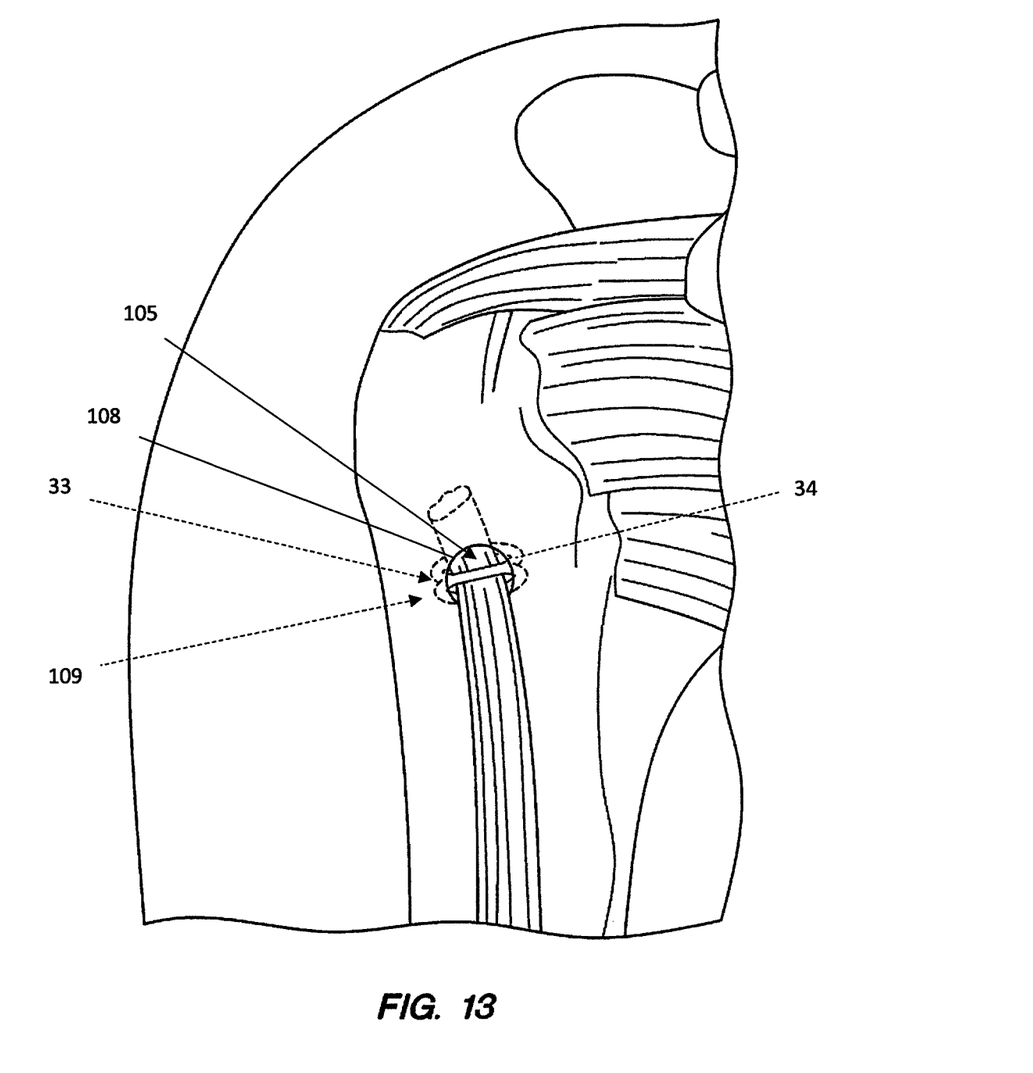
FIG. 13 demonstrates installation of the multi-opening implantable device crimp/tendon construct by rotating device 90 degrees to insert device into unicortical socket.

Another preferred embodiment of the implantable device is shown in FIGS. 10-13. In this embodiment the implantable device is comprised of multiple openings, which allow for a tendon/tissue to be passed through a first opening 31 and doubled back through at least a second opening 32. In this embodiment said device material is comprised of multiple interior borders 13 which define multiple interior openings. The multiple interior borders, which define the multiple openings can be connected via a common central connection 33 as shown in FIG. 10. This embodiment can be comprised of the shape of multiple oval rings connected via said common central connection 33. In this embodiment the implantable multi-opening device 30 can also be utilized for reattachment of the long head of the biceps tendon 100 to the proximal humerus 101 after tenotomy FIG. 2 in the shoulder joint. The typical steps include: (1) releasing the long head biceps 100 from the labrum arthroscopically (for tearing of the biceps, SLAP tear, subscapularis repair, or any other conditions treated with biceps tenodesis); (2) making a small incision and dissection to approach the intertubercular portion 102 of the humerus at the inferior margin of the pectoralis major; (3) Measuring the diameter 103 of the long head of the biceps tendon 100 at or just distal to the musculotendinous junction (anatomic studies suggest restoration of correct length by tenodesing the tendon near the musculotendinous junction at a location immediately proximal to the inferior border of the pectoralis major); (4) drilling 104 a corresponding unicortical socket 105 to match the tendon diameter 103 (FIGS. 3 and 10); (5) applying the implantable multi-opening device 30 to the long head of the biceps tendon 100 at the appropriate location by inserting said tendon through said first opening 31 and doubling said tendon back through said second opening 32 (FIG. 11); (6) crimping said implantable multi-opening device 30 with crimping pliers 20 to appropriate force (FIG. 12); (7) resecting 106 the remainder of the proximal tendon 107 (FIG. 7); and (8) inserting the multi-opening device 30 crimp/tendon construct 33 into the unicortical socket 105 by rotating the multi-opening device 30 crimp/tendon construct 33 90 deg. (FIG. 8) to clear the cortical wall 108 of the unicortical socket 105 and de-rotating the multi-opening device 30 crimp/tendon construct 33 to abut against the inner medullary wall 109 fixation surface (FIG. 9). Once inserted, the crimped multi-opening device 30 ends 34 are held against the fixation surface such as a medullary wall 109 by the resting tension of the fixated soft tissue.

While specific embodiments are provided herein, one skilled in the art would appreciate that the described device could be used for virtually any procedure requiring soft tissue fixation to bone or other soft tissue. Furthermore, one skilled in the art would appreciate that the described device could comprise any shape or size to accommodate different soft tissue morphology.

Another preferred embodiment is comprised of a crimping pliers 20 device designed to accept the described implantable device. Each opposing jaw surface 21 of said crimping pliers 20 is further comprised of a longitudinal recessed groove to accept the implantable device for crimping. In another embodiment, the longitudinal recessed groove will be sized to match the material diameter and length of the implantable device oval ring 10 or multi-opening device. The crimping pliers are comprised of a preset endpoint determined by implant device material composition, soft tissue diameter, and optimal compression force to provide sufficient force to crimp the implantable device securely to the soft tissue but prevent excessive force and tissue damage.

It is understood that the foregoing examples are merely illustrative of the present invention. Certain modifications of the articles and/or methods may be made and still achieve the objectives of the invention. Such modifications are contemplated as within the scope of the claimed invention.

What is claimed is:

1. A direct soft tissue implantable device comprising:
   any material structurally capable of resisting deformation once crimped;
   wherein said material comprises at least one interior border, where said interior border defines at least one interior opening, which accommodates a diameter of soft tissue;
   at least one exterior border, which is accommodated by a crimping pliers;
   wherein once crimped to said soft tissue, said device further comprises opposing ends, which extend perpendicularly from said soft tissue, which abut against a fixation surface; and
   wherein said opposing ends are held against said fixation surface by a resting tension of said soft tissue.

2. The direct soft tissue implantable device of claim 1 where said material is comprised of the shape of an oval ring.

3. The direct soft tissue implantable device of claim 2 where said oval ring is comprised of an incomplete oval.

4. The direct soft tissue implantable device of claim 1 where said material is comprised of the shape of a circular ring.

5. The direct soft tissue implantable device of claim 1 where said material is comprised of titanium.

6. The direct soft tissue implantable device of claim 1 where said material is comprised of stainless steel.

7. The direct soft tissue implantable device of claim 1 where said interior border is further comprised of texturing, studs, barbs, or similar means to increase purchase of said implantable device on said soft tissue once crimped.

8. The direct soft tissue implantable device of claim 1 where said exterior border is further comprised of texturing, studs, barbs, hooks, wings or similar means to increase purchase of said implantable device on a fixation surface.

9. The direct soft tissue implantable device of claim 1 where said material is comprised of multiple interior borders which define multiple interior openings, wherein said diameter of soft tissue passes through a first interior opening and said soft tissue doubles back through another of said interior openings.

10. The direct soft tissue implantable device of claim 9 where said multiple interior borders are connected via a common central connection.

11. The direct soft tissue implantable device of claim 10 where said material is comprised of at least two oval rings connected via a common central connection.

12. The direct soft tissue implantable device of claim 1 where said crimping pliers are comprised of two opposing jaw surfaces where said opposing jaw surfaces are each further comprised of a longitudinal recessed groove to accept said exterior border of said implantable device for crimping.

13. A method of reattaching soft tissue to bone utilizing the direct soft tissue implantable device of claim 1 comprising the steps of:
   (a) releasing soft tissue from its insertion or origin point;
   (b) making a small incision and dissection to approach a bone fixation point for site preparation;
   (c) Measuring the soft tissue diameter to be fixated;
   (d) drilling a corresponding unicortical socket in said bone fixation point to match the measured said soft tissue diameter;
   (e) applying said implantable device directly to said soft tissue at an appropriate location by inserting said soft tissue through said interior opening of said implantable device;
   (f) crimping said implantable device directly to said soft tissue with a crimping pliers to an appropriate force to create a crimp/soft tissue construct further comprising opposing ends which extend perpendicularly from said soft tissue;
   (g) resecting the remainder of proximal or distal soft tissue; and
   (h) inserting said crimp/soft tissue construct into said unicortical socket by rotating said crimp/soft tissue construct 90 deg. to clear a cortical wall of said unicortical socket and de-rotating said crimp/tendon construct to abut said opposing ends against a fixation surface of said bone fixation point;
   wherein said opposing ends are held against said fixation surface by a resting tension of said soft tissue.

14. The method of reattaching soft tissue to bone of claim 13 where said soft tissue is comprised of the long head of the biceps tendon.

15. The method of reattaching soft tissue to bone of claim 14 where the step of releasing soft tissue from its insertion or origin point is further comprised of releasing said long head biceps from a labrum arthroscopically.

16. The method of reattaching soft tissue to bone of claim 14 where the step of making a small incision and dissection to approach a bone fixation point for site preparation is further comprised of making a small incision and dissection to approach the intertubercular portion of the humerus at the inferior margin of the pectoralis major.

17. The method of reattaching soft tissue to bone of claim 14 where the step of measuring the soft tissue diameter to be fixated at or just distal to the musculotendinous junction is further comprised of measuring the diameter of the long head of the biceps tendon at or just distal to the musculotendinous junction.

18. The method of reattaching soft tissue to bone of claim 14 where said soft tissue diameter is the diameter of said long head of the biceps tendon.

19. The method of reattaching soft tissue to bone of claim 13 where said implantable device material is comprised of multiple interior borders which define multiple interior openings, wherein said soft tissue passes through each of said interior openings.

20. The method of reattaching soft tissue to bone of claim 19 where said multiple interior borders are connected via a common central connection.

21. The method of reattaching soft tissue to bone of claim 20 where the step of applying said implantable device to said soft tissue at the appropriate location is further comprised of inserting said soft tissue through a first interior opening and doubling said soft tissue back through a second interior opening.

\* \* \* \* \*